United States Patent [19]

Prockop

[11] 4,428,939
[45] Jan. 31, 1984

[54] COLLAGEN INHIBITING COMPOSITIONS AND PROCESSES FOR MANUFACTURING AND USING SAME

[76] Inventor: Darwin J. Prockop, 38 Turner Ct., Princeton, N.J. 08540

[21] Appl. No.: 311,920

[22] Filed: Oct. 16, 1981

[51] Int. Cl.³ .................... A61K 37/00; C07C 103/52
[52] U.S. Cl. .............................. 424/177; 260/112.5 R
[58] Field of Search .................. 424/177; 260/112.5 R

[56] References Cited

PUBLICATIONS

Chem. Abstr. vol. 96, (1982) 30237g.
Chem. Abstr. vol. 91, (1979) 121210f.
Chem. Abstr. vol. 85, (1976) 58322c.
Chem. Abstr. vol. 66, (1967) 72433d.
Chem. Abstr. vol. 71, (1969) 87910j.
Chem. Abstr. vol. 78, (1973) 30246n.

*Primary Examiner*—Delbert R. Phillips
*Attorney, Agent, or Firm*—Louis E. Marn; Elliot M. Olstein

[57] ABSTRACT

There is disclosed the use of a collagen inhibiting composition including in polymeric form select analogs of proline and processes for the manufacture and use of such a collagen-inhibiting composition to reduce scar tissue formation.

4 Claims, No Drawings

4,428,939

COLLAGEN INHIBITING COMPOSITIONS AND PROCESSES FOR MANUFACTURING AND USING SAME

FIELD OF THE INVENTION

This invention relates to pharmaceutical compositions and processes for manufacturing same, and more particularly to the manufacture and use of certain analogs of the amino acid proline in complex polymeric form for controlling the cellular synthesis of scars and fibrous tissue in animals.

BACKGROUND OF THE INVENTION

Collagen is a protein which occurs naturally in all animals in the form of tough fibers. Such collagen fibers are in effect the "glue" holding together the tissues of the body. Collagen is synthesized by many cells from certain amino acid including the amino acid proline. Collagen-producing cells are located primarily in the skin, bone, tendons, ligaments, nerves, cartilage and blood vessels of animals and collagen fibers are formed whenever tissue is damaged, in the sense that deposition of collagen fibers is a normal part of the process of tissue repair. In certain instances, however, excessive amounts of collagen are produced, with substantial, undesirable results. In particular, scar formation in the healing of wounds, from trauma or disease, or following surgery, is a result of excessive production of collagen, since the major constituent of scar tissue is collagen.

The development of large, unsightly masses of scar tissue may produce psychological problems in human beings, and may interfere substantially with the normal physical and biological function of organs and tissues. For example, after surgery to the abdomen, the formation of excessive scar tissue or "adhesions" around abdominal organs, such as the intestines, often interferes with the functionality of such organs and may cause severe pain and even death. After hand surgery, the formation of excessive scar tissue around the tendons of the wrist or hand often prevents normal functioning of the hand. After surgery to the back, excessive scar tissue around the spinal nerves may produce severe pain and limitation of motion. After plastic surgey to the face, the formation of excessive scar tissue may frequently compromise the benefits of the surgery.

In horses, a condition known as "proud flesh" often occurs. It is an excessive build-up of scar tissue and when occuring near a leg joint may interfere considerably with the use of the legs for heavy work or for racing. Similar excessive build-up of scar tissue may also occur in horses when leg tendons are surgically repaired.

It is, therefore, desirable to be able to control or limit the amount of collagen formed and released by the collagen-producing cells in specific body areas for limited periods of time. However, in controlling the synthesis and deposition of collagen fibers, it is extremely important not to interfere with the cellular production of other protein necessary for normal body functioning.

In U.S. Pat. No. 151,986 filed June 10, 1971, (now abandoned) but issued as Belgium Patent No. 784,650, there is disclosed the use of free proline analogs in a pharmaceutically acceptable carrier for controlling collagen formation. The use of such proline analog exhibited some efficacy in reducing scar tissue formation, however, the benefit was at best minimal. Such free proline analogs are not susceptible to topical application about a wound, since topical application results in an edematose condition, i.e. the accumulation of fluid with concomitant symptons of pain and swelling. Further, free proline analogs are water soluble and readily absorbed thereby entering the circulation system.

OBJECTS OF THE INVENTION

An object of the present invention is to provide a novel composition including in polymeric form select analogs of proline for limiting and controlling collagen synthesis.

Another object of the present invention is the topical application of an effective amount of a novel composition including in polymeric form select analogs of proline for limiting and controlling collagen synthesis.

Yet another object of the present invention is to provide a process for preparing a novel composition including in polymeric form select analogs of proline for limiting and controlling collagen synthesis.

Still another object of the present invention is to provide novel collagen-inhibiting compositions including in polymeric form select analogs of proline for localized application to animals for the purpose of limiting and controlling the synthesis and deposition of collagen fibers.

A still further object of the present invention is to provide a method for the prevention and control of certain conditions in animals involving the excessive synthesis and deposition of collagen fibers comprising the administration of an effective amount of a collagen-inhibiting composition including in polymeric form select proline analogs.

Yet another object of the present invention is to provide certain collagen-inhibiting compositions and methods to be used in treating animals to control and limit scar tissue formation due to wounds from trauma, including burns or diseases, after surgery, for the treatment of those diseases involving fibrosis, with excessive accumulations of collagen, such as pulmonary fibrosis, etc.

SUMMARY OF THE INVENTION

These and other objects of the present invention are achieved by the use of a collagen-inhibiting composition including in polymeric form select analogs of proline and processes for the manufacture and use of such a collagen-inhibiting composition.

DETAILED DESCRIPTION OF THE PRESENT INVENTION

As used herein, the term "quasi-collagen" means a collagen-like protein molecule which includes a proline analog, at one or more of the sites at which proline or trans-4-hydroxy-L-proline would normally be found in collagen.

As used herein, the term "animals" includes human beings.

As used herein, the term "polymers" includes compounds of large molecular weight and which consists of proline analogs together with amino acids or similar compounds, linked to each other by peptide bonds, ester bonds, or other covalent bonds.

While not fully understood, it is believed that the topical use of such a collagen-inhibiting composition including in polymeric form select proline analogs of the present invention, such as the application of such composition in powdered form to the area to be treated, results in the gradual decomposition of such a polymeric proline analog composition through the action of either water found in tissue fluids, or through the action of degradative enzymes naturally present in tissue fluids. In the course of decomposing, such a collagen-inhibiting composition releases one or more proline analogs, together with other compounds which have no appreciable biological effects. The thus released proline analog or proline analogs will be taken up by the collagen-producing cells in the area and will be incorporated into some of the collagen molecules synthesized within the cell to form "quasi-collagen" molecules. Of the 3,000 amino acids which are incorporated into a single normal collagen molecule, about 600 of the amino acid sites are occupied by proline and by trans-4-hydroxy-L-proline, an amino acid form from proline during the synthesis of collagen.

Accordingly, when a proline analog is administered into the collagen-producing cells "quasi-collagen" molecules are synthesized by the cells, incorporating the proline analog at certain sites at which proline or trans-4-hydroxy-L-proline is normally present in a collagen-molecule. The number of sites at which the proline analog is present will vary from a few sites in each molecule to more than one-half of the available proline or trans-4-hydroxy-L-proline sites. These "quasi-collagen" molecules do not have the normal three-dimensional conformation of normal collagen and therefore cannot be used by the cells and tissues to assemble collagen fibers. Therefore, the net effect of incorporation of the proline analogs is to inhibit synthesis of collagen fibers. The duration of such inhibition of collagen formation depends on such factors as the particular proline analog administered, the quantity administered, the rate at which the proline analog is released from the collagen-inhibiting composition, and the frequency of dosage repetition.

The inhibition of the formation of collagen fibers by the synthesis of the "quasi-collagen" is believed to occur for the following reasons. In a normal collagen molecule, the amino acids proline annd trans-4-hydroxy-L-proline account for approximately 20% of the total amino acid composition. The presence of proline and trans-4-hydroxy-L-proline in the three polypeptide chains which comprise the collagen molecule is apparently essential for the three chains to fold into a helical, rope-like three-dimensional structure of the normal collagen molecule. Incorporation of proline analogs into the collagen molecule in sites normally occupied by proline and trans-4-hydroxy-proline residues prevents the three polypeptide chains from assuming the normal helical conformation, for one or two reasons. One reason is that the proline analogs, because of incorrect steric or chemical structure, do not allow the three polypeptide chains to come together correctly. The second reason is that, with several proline analogs, the presence of the proline analogs in the polypeptide chains prevent the normal conversion of specific proline residues to trans-4-hydroxy-L-proline residues by the action of an enzyme normally present in collagen-synthesizing cells. Because the conversion of proline to trans-4-hydroxy-L-proline does not occur to an adequate extent, the three polypeptide chains cannot form a helical structure which is stable under normal body conditions. Since the cells synthesize "quasi-collagen" instead of normal collagen, the production of collagen molecules used to form fibers is marketedly reduced.

The proline analogs which are useful in the practice of the present invention include the cis-isomer of proline analogs having cis- and trans-isomers, and not the transisomers; and the laevo isomers of proline analogs, and not the dextro isomers or non-optical isomers, except where the DL form is required to be used since the L form cannot be economically isolated.

Proline analogs of the present invention include the cis- and laevo isomers of the compounds of the general structural formula

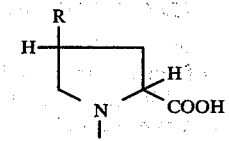

wherein R is OH, Cl, F, CH$_3$, NH$_3$, OC(O)CH$_3$, OC(OH)CH$_2$, CH$_3$, SH, SCH$_3$, OCH$_3$, ONO$_2$, OSO$_3$H, H$_2$PO$_4$, or COOH; L-pipecolic acid; 1,2,3,6-tetrahydro-L-picolinic acid; 1,2,3,4-tetrahydro-L-picolinic acid; 1,4,5,6-tetrahydro-L-picolinic acid; 1,2,5,6-tetrahydro-L-picolinic acid; and 1,2-dihydro-L-picolinic acid; the laevo isomers of the compound of the general structural formula

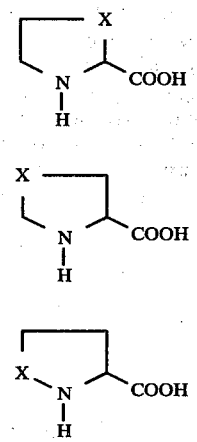

where X is N, S or O; L-azetidine-2-carboxylic acid, 3,4-dehydro-L-proline and 4,5-dehydro-L-proline.

The proline analogs which are preferred for use in the a collagen-inhibiting compositions of the present invention are L-azetidine-2-carboxylic acid, cis-4-fluoro-L-proline, 3,4-dehydro-L-proline, cis-4-hydroxy-L-proline and cis-4-chloro-L-proline with cis-4-hydroxy-L-proline being most preferred.

The proline analogs are employed in a collagen-inhibiting composition in which the proline analog is chemically linked into a large molecular structure and from which the proline analog is slowly released when the composition is topically applied. One collagen-inhibiting composition consists of a polymer of cis-hydroxy-L-proline chemically linked to itself by ester bonds resulting in a large molecular structure of the formula:

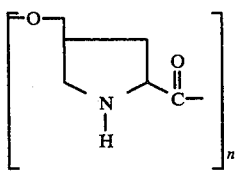

Another composition consists of polypeptide chains of amino acid to which a proline analog is linked through the carboxyl group of the proline analog to form an ester linkage to a hydroxyl group of a polypeptide chain. For example, a polymeric structure given by the structural formula:

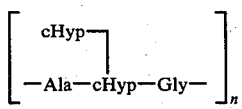

where cHyp is cis-4-hydroxy-L-proline, Ala is L-alanine and Gly is glycine.

It is important to note that the compositions including the proline analogs of the present invention are of large molecular weight and thereby will not readily leave the site in or on administered tissues. Also the collagen-inhibiting composition do not have strong osmotic effects as might be obtained with small molecular weight compounds, such as proline analogs, per se. It is important to note that the polymers hydrolyzed by the action of water per se, or by the action of water in the presence of naturally occurring tissue enzymes, to slowly release the proline analog to the collagen-producing cells. The controlled release of the proline analog in such manner permits the administering of large concentrations of the proline analog at the site where its action is required.

As a proline analog is released from the polymer composition and diffuses from the administered site, the proline analog is rapidly diluted by body fluids and its concentration diminished. Therefore, tissues or sites other than the administered site are exposed to much lower concentrations of the proline analog and thereby markedly diminish any possible deleterious effects on other tissues. Thus, the use of the collagen-inhibiting composition of the present invention functions to modulate the production of collagen fibers by collagen-producing cells within given sites of animals.

The mechanism of "quasi-collagen" formation, while significantly curtailing for a period of time synthesis of collagen and collagen fibers by individual collagen-producing cells, does not interfere with the production of other proteins by these same cells or by non-collagen-producing cells. This is very important for the effective functioning for limiting or for the controlled production of collagen since in the usual situation, agents interfering with the synthesis of protein by one type of animal cell in one site within a tissue will interfere with a synthesis of all proteins in all the tissues of the animal, thereby producing a wide range of systemic effects, many of which can be harmful.

As is hereinafter more fully discussed, the collagen-inhibiting compositions of the instant invention have efficacy in inhibiting formation of fibrous tissue in laboratory animals, and are therefore considered to be useful in controlling the formation of scar tissue in wounds, caused by trauma, disease, or surgical incisions in animals, while permitting growth of normal tissues. In the use of the disclosed collagen-inhibiting compositions to prevent scar tissue formation, a limited amount of the collagen-inhibiting compositions of the present invention are locally applied in a single application, or for a limited period of time, until a significant healing of the tissue has occurred, after which no further application of the collagen-inhibiting composition is necessary. The use of a collagen-inhibiting composition of the present invention to prevent scar formation, does not necessarily terminate the synthesis of collagen fibers by collagen-producing cells. Rather, by the proper control of dosage amount and dosage frequency, the collagen-producing cells can be permitted to continue to synthesize limited amounts of collagen for normal tissue-adhesive function.

Controlling scar formation has particular application to humans and several other species of animals, the members of which have a tendency to excessive collagen accumulation in the form of scars at sites of wound, surgical incisions, or tissue damage produced by a variety of agents. The application includes especially certain racial groups among humans, having a genetic tendency to keloid formation at the sites of wounds or incisions. The collagen-inhibiting compositions may be utilized for the prevention of excessive deposition of collagen in diseased conditions in which non-collagenous tissues are replaced by collagen. An example of the excessive deposition of collagen in certain disease conditions to which the collagen-inhibiting compositions of the present invention are applicable is lung fibrosis, a condition caused by inhalation of foreign materials such as silica or asbestos, or as occurs in older persons from unknown causes. In such instances, where a lung fibrosis is commencing, further progression is prevented by administration of the collagen-inhibiting compositions in the form of aerosols. In other instances the collagen-inhibiting compositions are applied directly to the site at which control of collagen deposition and scarring is desired.

As hereinabove described, the most preferred proline analog for use in the collagen-inhibiting composition, is cis-4-hydroxy-L-proline. Cis-4-hydroxy-L-proline is commercially available in limited quantities and is naturally present, e.g. extractable from the leaves and pericarp of a species of sandalwood tree, *Santalum album*, common to India. Cis-4-hydroxy-L-proline is found in these leaves in the natural form and is capable of being extracted by the processing disclosed in 80 *Biochemical Journal* 378 (1961) and 58 *Biochemical Journal* 57 (1954). Cis-4-fluoro-L-proline may be synthesized by the procedures disclosed in 4 *Biochemistry* 2507 (1965). L-azetidine-2-carboxylic acid may be extracted from the leaves of Lily-of-the Valley by the procedure disclosed in 64 *Biochemical Journal* 323 (1956). 3,4-Dehydro-L-proline may be synthesized by the procedure disclosed in 84 *Journal of the American Chemical Society* 1967 (1962).

There follows certain examples which illustrate in detail the process of this invention for the purpose of controlling the synthesis of collagen fibers in animals, as well as procedures for preparing a number of representative dosage forms thereof.

EXAMPLE I

To demonstrate the effectiveness of the collagen-inhibiting compositions herein described, a test system consisting of cells from normal human skin is employed. The principle of the test system is that when collagen-producing cells, such as normal skin fibroblasts are introduced into a plastic flask containing a nutrient medium, the cells attach to the surface of the flask and grow. However, firm attachment of normal fibroblasts to the surface of the flask requires that the cells first synthesize a "pad" comprised of collagen fibers and several other materials through which the collagen producing cells attach to the plastic surface. If synthesis of normal collagen fibers is prevented, the collagen-producing cells, such as the normal skin fibroblasts, will not attach and therefore will not grow. In the present test system, cis-4-hydroxy-L-proline prevents attachment and growth of normal fibroblasts since cis-4-hydroxy-L-proline promotes the synthesis of "quasi-collagen". The manner in which cis-4-hydroxy-L-proline produces these effects has been disclosed in 336 Biochimica et Biophysica Acta 234, (1974); 174 Archives of Biochemistry and Biophysics 381 (1976); 266 Nature 63 (1977); and 272 Nature 622 (1978).

The following three polymeric collagen-inhibiting compositions of the present invention are tested: cH-I, a polyester of cis-4-hydroxy-L-proline prepared by the polymerization of an active ester of a diester of cis-4-hydroxy-L-proline; cH-II, a polyester of cis-4-hydroxy-proline prepared by the polymerization of an active ester; and cHAG, a polymer in which cis-4-hydroxy-L-proline is ester-linked to cis-4-hydroxy-L-proline in a polypeptide chain formed from cis-4-hydroxy-L-proline, alanine and glycine.

None of the three polymeric compositions are soluble in water and are consequently dissolved in 50% acetic acid and water. The solution is placed dropwise on a microscopic coverslip and the solvent evaporated with warm air from a hair dryer. The coverslip, coated with the composition, is then placed in a pastic culture flask (75 cm$^2$; Falcon). From $5 \times 10^5$ to $10.5 \times 10^5$ normal human fibroblasts in 2 ml of cell culture medium are added to the flask. The flask is incubated at 37° C. in 5% carbon dioxide and 95% air for 3 to 5 days, and the number of cells in the flask counted. Control sample contained microscopic coverslips treated with an equal volume of solvent and air-dried.

All three of the compositions inhibited growth of the fibroblasts. cH-I, at a dosage level equivalent to 500 μg/ml, totally prevented growth, and fewer cells are recovered at the end of the growth period than are initially added to the flask (Experiment #1 in Table I). cH-II and cHAG inhibited growth at dosage levels equivalent to 300 and 500 μg/ml (Experiment #2 and #3 in Table I).

TABLE I

Effect of Compositions on Collagen Synthesis as Assayed by Attachment and Growth of Human Skin Fibroblast in Plastic Culture Flasks

| Expt. # | Treatment | Dosage Level (μg/ml) | Cells per flask ($\times 10^5$) Initial | Final |
|---|---|---|---|---|
| 1 | None | | 5.0 | 67 |
| | cis-4-Hydroxy-L-proline | 250 | 5.0 | <1 |
| | cH-I | 500 | 5.0 | 1.0 |
| 2 | None | | 10.3 | 98 |
| | cis-4-Hydroxy-L-proline | 100 | 10.3 | 2.2 |
| | cH-II | 300 | 10.3 | 28 |
| | cH-II | 500 | 10.3 | 7.0 |
| | cHAG | 300 | 10.3 | 10.0 |
| 3 | None | | 7.0 | 56 |
| | cis-4-Hydroxy-L-proline | 50 | 7.0 | 12 |
| | cis-4-Hydroxy-L-proline | 150 | 7.0 | 1.3 |
| | cHAG | 100 | 7.0 | 14.5 |

TABLE I-continued

Effect of Compositions on Collagen Synthesis as Assayed by Attachment and Growth of Human Skin Fibroblast in Plastic Culture Flasks

| Expt. # | Treatment | Dosage Level (μg/ml) | Cells per flask ($\times 10^5$) Initial | Final |
|---|---|---|---|---|
| | cHAG | 300 | 7.0 | 7.0 |

In a parallel series of experiments, coverslips containing cH-II are placed in culture flasks with fibroblasts under the same conditions. After 1, 2, 3 and 4 days, the coverslips are removed, and the composition remaining on the coverslip chemically assayed for content of cis-4-hydroxy-L-proline. The results indicated that the composition disappeared from the cover-slip with a half-life of about 24 hours. Therefore, this is about the rate at which cis-4-hydroxy-L-proline is released from the polymer under the conditions of this experiment.

To establish that the effects of the collagen-inhibiting compositions are specific for collagen-producing cells, similar experiments are carried out with a line of cultured cells which do not produce collagen. As disclosed in 266 Nature 63 (1977), the growth of such cells is not inhibited by cis-4-hydroxy-L-proline. Neither the polyester cH-I nor the polymer cHAG significantly inhibited the growth of the cells (Table II).

TABLE II

Effects of Compositions on Attachment and Growth of KB Cells.

| Treatment | Dosage Level (μg/ml) | Cells per flask ($\times 10^5$) Initial | Final |
|---|---|---|---|
| None | | 8.0 | 29 |
| cH-I | 500 | 8.0 | 24 |
| cHAG | 500 | 8.0 | 27 |

EXAMPLE 2

To demonstrate the effectiveness in vivo of the pharmaceutical compositions disclosed here, the polyester cH-II is dissolved in acetic acid and placed dropwise on polyvinyl sponges. The solvent is evaporated from the sponges with a hair dryer and the sponges implanted subcutaneously in rats.

After 4 days, the sponges are removed. Fibrous capsule had formed around the sponge and the sponge lyophilized and weighed. As indicated in Table III, 2.5 mg of the polyester cH-II on the sponges did not have a statistically significant effect on the dry weight of the fibrous capsule. Placing 5.0 mg of cH-II on the sponge significantly decreased the amount of fibrous capsule.

TABLE III

Effect of a Polyester of cis-4-hydroxy-L-proline in Rats.

| Composition placed in sponge | # of rats[a] | Dose (mg/sponge) | Weight gain of sponge (mg) Untreated | Treated | Difference[b] |
|---|---|---|---|---|---|
| Control | 4 | | 28.33 | 27.17 | −1.16 |
| cH-II | 4 | 2.5 | 31.49 | 29.32 | −2.17 |
| cH-II | 4 | 5.0 | 33.75 | 27.91 | −5.84[c] |

[a]Dry weights of sponges were assayed before and after implantation. Two sponges were placed in each rat, one treated and one untreated. In control, the treated sponge was impregnated with the amount of acetic acid necessary to impregnate sponges with 5 mg of cH-II.
[b]Values indicate means of weight gains in treated and untreated sponges expressed as mg dry weight.
[c]Difference in mean change in dry weight is significant at p <.05 by student's t-test.

EXAMPLE III

The polymer cH-I is synthesized by polymerization of an active diester at room temperature and under atmospheric pressure. The starting material is Z-cHyp-OPcp, N-benzyloxycarbonyl-(Z-) and O-pentachlorophenyl-(-OPcp) substituted derivative of cis-4-hydroxy-L-proline (cHyp). Z-cHyp-OPcp (5 g, 9.7 mmoles) is dissolved in 50 ml of dichloromethane and reacted with 150 ml of isobutylene and 0.5 ml of concentrated $H_2SO_4$ at room temperature for 4 days. The solution is neutralized with triethylamine and evaporated in vacuo. The residue is dissolved in chloroform and washed with 5% sodium bicarbonate and water. The chloroform layer is dried over sodium sulfate and evaporated under reduced pressure. The crystalline residue is recrystallized from methanol to yield 5.05 g. The product Z-cHyp (Bu$^t$)-OPcp (2.28 g, 4 mmoles), thus obtained is dissolved in 4 ml of dimethyl formamide and then Z-cHyp-OH (1.06 g, 4 mmoles), triethylamine (0.56 ml, 4 mmoles) and imidazole (272 mg, 4 mmoles) are added. The mixture is left to stand at room temperature for 2 days, evaporated in vacuo, and the residue is purified by silica-gel column chromatography to obtain an oily product.

The product thus obtained is dissolved in 30 ml of ethyl-acetate and 30 ml of tetrahydrofuran, and pentachlorophenol (931 mg, 3.5 mmoles) and dicyclohexylcarbodiimide (721 mg, 3.5 mmoles) are added. The mixture is allowed to stand for 15 hr, and the precipitate is removed by filtration and the solution is evaporated. The residue is recrystallized from chloroform and methanol. The yield is 2.17 g. The product thus obtained is treated with tri-fluoroacetic acid for 60 min, and then evaporated. The residue is polymerized by dissolving in 4 ml of dimethylformamide with triethylamine, and imidazole (170 mg, 2.5 mmole) for 7 days. The solution is evaporated. The residue is dissolved in 30 ml of acetic acid and 30 ml of methanol and subjected to catalytic hydrogenation over palladium-charcoal for 8 hrs. The catalyst is removed by filtration and the filtrate concentrated. The residue is dissolved in dichloromethane and ether is added to give 390 mg of amorphous powder.

EXAMPLE IV

The polymer cH-II is synthesized by polymerization of an active ester with imidazole at elevated temperature and under reduced pressure. Z-cHyp-OPcp (3 g, 5.8 mmoles) is dissolved in 2 ml of dimethylformamide and reacted with 5 molar equivalents of imidazole at 110° C. in vacuo for 7 days. The oily precipitate obtained is washed with methanol to remove excess imidazole, and is then dissolved in 10 ml of dimethylformamide. The solution is saturated with anhydrous ammonia to amidate the carboxyl-terminal residue, and evaporated. The residue is dissolved in acetic acid and dimethylformamide, and subjected to catalytic hydrogenation over palladium-charcoal for 2 days. The catalyst is removed by filtration and the filtrate is concentrated. The residue is dissolved in acetic acid and dialyzed against 50% of acetic acid for 1 day. The contents of the bag are lyophilized to give 1.8 g of amorphous powder.

EXAMPLE V

The polymer cHAG is synthesized from N-benzyloxycarbonyl-substituted cHyp (Boc-cHyp-OH) and L-alanine (Boc-Ala-OH), and from O-benzyl-glycine (GlyOBzl). To a solution of GlyOBzl.p-toluenesulphonyl (1.3 g, 4 mmoles) and triethylamine (0.56 ml, 4 mmoles) in 10 ml tetrahydrofuran, Boc-cHyp-OH (0.85 g, 3.7 mmoles) and dicyclohexylcarbodiimide (0.76 g, 3.7 mmoles) are added. The mixture is allowed to react for 15 hr. The precipitate is removed by filtration and the filtrate is concentrated to a residue which is then dissolved in ethylacetate. The solution is washed with N-hydrochloric acid, 5% sodium bicarbonate, and water. It is dried over sodium sulfate and evaporated in vacuo. The residue is recrystallized from ethylacetate and n-hexane to obtain 1.02 g.

The product thus obtained is treated with trifluoroacetic acid for 40 min and evaporated. The residue is dissolved in 3 ml of dimethylformamide, and triethylamine and the N-hydroxy-succinimide derivative of Boc-Ala-OH, Boc-Ala-OSu (715 mg, 2.5 mmoles), are added. The mixture is allowed to react for 2 days and evaporated. The residue is dissolved in ethylacetate and the solution is washed with 1 N HCl, 5% sodium bicarbonate, and water. It is dried over sodium sulfate and evaporated. The residue is recrystallized from ethylacetate and n-hexane to obtain 950 mg. The product obtained is dissolved in methanol and subjected to catalytic hydrogenation over palladium-charcoal for 6 hrs. The catalyst is removed by filtration and the filtrate is concentrated to a residue which is recrystallized from ethylacetate and n-hexane to yield 840 mg.

The product is dissolved is 5 ml of dimethylformamide, and Z-cHp(But)-OPcp (1.31 g, 2.3 mmole) and imidazole (96 mg, 2.3 mmole) are added. The mixture is allowed to react for 2 days, evaporated in vacuo, and the residue is purified by column chromatography on silica gel to yield 940 mg.

The product is dissolved in 10 ml of ethylacetate and 10 ml of tetrahydrofuran, and Pcp-OH (373 mg, 1.4 mmole) and dicyclohexylcarbodiimide (310 mg, 1.5 mmole) are added. The mixture is allowed to react for 15 hr, and evaporated in vacuo. The residue is purified by column chromatography to yield 1.0 g.

The product thus obtained is treated with trifluoroacetic acid for 40 min and evaporated in vacuo. The residue is polymerized by dissolving 2 ml of dimethylformamide and triethylamine for 7 days and evaporated in vacuo. The residue is dissolved in 10 ml of acetic acid and 10 ml of methanol, and subjected to catalytic hydrogenation over palladium-charcoal for 6 hrs. The catalyst is removed by filtration and filtrate is concentrated. The sample is then dissolved in acetic acid and dialyzed against water for 1 day to obtain 140 mg. of amorphous powder.

While the invention has been described in connection with several exemplary embodiments thereof, it will be understood that many modifications will be apparent to those of ordinary skill in the art; and that this application is intended to cover any adaptations or variations thereof. Therefore, it is manifestly indended that this invention be only limited by the claims and the equivalents thereof.

What is claimed:

1. A composition for the control of the cellular synthesis of collagen fibers in animals, which comprises a proline analog in polymeric form selected from the group, consisting of L-azetidine-2-carboxylic acid; cis-4-hydroxy-L-proline; 3,4-dehydro-L-proline; cis-4-hydroxy-L-proline; cis-4-chloro-L-proline; laevo and cis isomers of compounds of the general structural formula

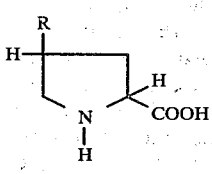

wherein R is OH, Cl, F, NH₂, CH₃, OC(O)CH₃, OC-(O)CH₂CH₃, SH, SCH₃, OCH₃, ONO₂, OSO₃H, H₂PO₄, or COOH; L-pipecolic acid; 1,2,3,6-tetrahydro-L-picolinic acid; 1,2,3,4-tetrahydro-L-picolinic acid; 1,4,5,6-tetrahydro-L-picolinic acid; 1,2,5,6-tetrahydro-L-picolinic acid; 1,2-dihydro-L-picolinic acid; laevo isomers of the compound of the general structural formula

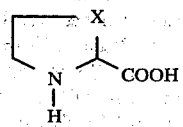

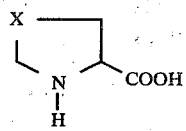

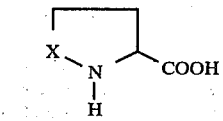

where X is N, S or O; or mixture thereof and a pharmaceutically acceptable carrier therefor.

2. The composition as defined in claim 1 wherein said proline analog is cis-4-hydroxy-L-proline.

3. A method for the synthesis of polymer of any of the proline analogs defined in claims 1 or 2 wherein the proline analogs are linked through ester bonds to a polypeptide chain.

4. A method for the control of the cellular synthesis of collagen fibers in animals in an area where scar tissue formation can occur, which comprises the topical application of an effective amount of the composition as defined in claims 1 or 2 in said area.

* * * * *

UNITED STATES PATENT AND TRADEMARK OFFICE
CERTIFICATE OF CORRECTION

PATENT NO. : 4,428,939
DATED : January 31, 1984
INVENTOR(S) : Darwin J. Prockop

It is certified that error appears in the above-identified patent and that said Letters Patent is hereby corrected as shown below:

On the title page insert:

-- /73/ Assignee: College of Medicine and Dentistry of New Jersey --.

Signed and Sealed this

Fifteenth Day of January 1985

[SEAL]

Attest:

GERALD J. MOSSINGHOFF

*Attesting Officer*  *Commissioner of Patents and Trademarks*